US010684288B2

(12) United States Patent
Anderson et al.

(10) Patent No.: US 10,684,288 B2
(45) Date of Patent: Jun. 16, 2020

(54) FAST METHOD TO ANALYSE BLOOD SAMPLES FOR THE IDENTIFICATION OF HEMOGLOBIN VARIANTS USING ELECTRON TRANSFER DISSOCIATION

(71) Applicant: Micromass UK Limited, Wilmslow (GB)

(72) Inventors: Malcolm Anderson, Sale (GB); Jeffery Mark Brown, Hyde (GB); Jonathan Williams, Neath (GB)

(73) Assignee: MICROMASS UK LIMITED, Wilmslow (GB)

( * ) Notice: Subject to any disclaimer, the term of this patent is extended or adjusted under 35 U.S.C. 154(b) by 109 days.

(21) Appl. No.: 15/128,198

(22) PCT Filed: Mar. 31, 2015

(86) PCT No.: PCT/GB2015/050990
§ 371 (c)(1),
(2) Date: Sep. 22, 2016

(87) PCT Pub. No.: WO2015/150785
PCT Pub. Date: Oct. 8, 2015

(65) Prior Publication Data
US 2017/0131290 A1 May 11, 2017

(30) Foreign Application Priority Data

Mar. 31, 2014 (EP) ..................................... 14162941
Mar. 31, 2014 (GB) ................................... 1405782.2

(51) Int. Cl.
*G01N 33/68* (2006.01)
*G01N 33/72* (2006.01)
*H01J 49/00* (2006.01)

(52) U.S. Cl.
CPC ....... *G01N 33/6848* (2013.01); *G01N 33/721* (2013.01); *G01N 33/726* (2013.01); *H01J 49/0031* (2013.01); *H01J 49/0072* (2013.01)

(58) Field of Classification Search
CPC ............. G01N 33/6848; G01N 33/726; G01N 33/721; H01J 49/0072; H01J 49/0031
See application file for complete search history.

(56) References Cited

U.S. PATENT DOCUMENTS

| 6,447,665 B1 * | 9/2002 | Johnson | C25D 11/18 |
| | | | 148/272 |
| 2006/0138320 A1 * | 6/2006 | Bateman | H01J 49/0031 |
| | | | 250/288 |

FOREIGN PATENT DOCUMENTS

| TW | 201211543 | 3/2012 |
| WO | 2004/090552 | 10/2004 |

OTHER PUBLICATIONS

Beardsley, RL et al. Non-covalent protein tetramers and pentamers with "n" charges yield monomers with n/4 and n/5 charges. Analytical Chemistry. 2009. 81(4): 1347-1356. (Year: 2009).*
Chalkley, RJ et al. Statistical analysis of peptide electron transfer dissociation fragmentation mass spectrometry. Analytical Chemistry. 2010. 82: 579-584. (Year: 2010).*
Li, W et al. ETD fragmentation features improve algorithm. Expert Rev. Proteomics. 2012. 9(3): 241-243. (Year: 2012).*
Wysocki, VH et al. Mass spectrometry of peptides and proteins. Methods. 2005. 35: 211-222. (Year: 2005).*
Kebarle, P et al. Electrospray: From ions in solution to ions in the gas phase, what we know now. Mass Spectrometry Reviews. 2009. 28: 898-917. (Year: 2009).*
Loo, JA. Electrospray ionization mass spectrometry: a technology for studying noncovalent macromolecular complexes. International Journal of Mass Spectrometry. 2000. 200: 175-186. (Year: 2000).*
Green, BN et al. Electrospray ionization mass spectrometric determination of the molecular mass of the ~200-kDa globin dodecanner subassemblies in hexagonal bilayer hemoglobins. The Journal of Biological Chemistry. 1999. 274(40): 28206-28212. (Year: 1999).*
Pacholarz, KJ et al. Mass spectrometry based tools to investigate protein-ligand interactions for drug discovery. Chem. Soc. Rev. 2012. 41: 4335-4355. (Year: 2012).*
Lermyte, Frederik et al., "ETD Allows for Native Surface Mapping of a 150 kDa Noncovalent Complex on a Commercial Q-TWIMS-TOF Instrument", J. Am. Soc. Mass Spectrom, No. 25, pp. 343-350, May 2014.
Acosta-Martin et al., "Quantitative Mass Spectromony Analysis of Intact Hemoglobin A2 by Precursor Ion Isolation and Detection", Analytical Chemistry, vol. 85, No. 16, pp. 7971-7975, 2013.
Catherman et al., "Top Down Proteomics: Facts and Perspectives", Biochemical and Biophysical Research Communications, vol. 445, No. 4, pp. 683-693, Feb. 17, 2014.
Edwards et al., "Top-Down Proteomics and Direct Surface Sampling of Neonatal Dried Blood Spots: Diagnosis of Unknown Hemoglobin Variants", Journal of American Society for Mass Spectronomy, vol. 23, No. 11, pp. 1921-1930, 2012.
Graca et al., "Electron Transfer Dissociation Mass Spectronomy of Hemoglobin on Clinical Samples", Journal of American Society for Mass Spectronomy, vol. 23, No. 10, pp. 1750-1756, 2012.
Wild et al., "Rapid Identification of Hemoglobin Variants by Electrospray Ionization Mass Spectronomy", Blood Cells, Molecules and Diseases, vol. 27, No. 31, pp. 691-704, May 2001.
Williams, "Identification of Human Hemoglobin Protein Variants Using Electrospray Ionization-Electron Transfer Dissociation Mass Spectronomy Application Benefits", Waters—Application note, pp. 1-5, Apr. 1, 2012, Retrieved on Internet Oct. 2, 2014, from: URL:http://www.waters.com/waters/library.htm?cid=511436&lid=134673290.

* cited by examiner

*Primary Examiner* — Susan E. Fernandez
(74) *Attorney, Agent, or Firm* — Womble Bond Dickinson (US) LLP; Deborah M. Vernon; Heath T. Misley (57) ABSTRACT

A method of screening or testing a sample is disclosed that comprises ionising a native human hemoglobin sample to generate parent or precursor ions, subjecting the parent or precursor ions to Electron Transfer Dissociation fragmentation so as to generate a plurality of fragment ions, mass analysing the fragment ions and determining whether or not the fragment ions include fragment ions which are indicative of a variant of hemoglobin.

18 Claims, 6 Drawing Sheets

Fig. 4 Partial mass spectra of normal (HbAA) and sickle varient (HbAS) hemoglobin. The peak with a mass difference of -30Da from normal at m/z 664.5 can be identified as that of sickle hemoglobin Fig. 5  Partial Zoom mass spectra of normal (HbAA) and sickle varient (HbAS) hemoglobin. The peak with a mass difference of -30Da from normal at m/z 664.5 can be identified as that of sickle hemoglobin

FAST METHOD TO ANALYSE BLOOD SAMPLES FOR THE IDENTIFICATION OF HEMOGLOBIN VARIANTS USING ELECTRON TRANSFER DISSOCIATION

CROSS REFERENCE TO RELATED APPLICATION APPLICATIONS

This application is the National Stage of International Application No. PCT/GB2015/050990, filed 31 Mar. 2015 which claims priority from and the benefit of United Kingdom patent application No. 1405782.2 filed on 31 Mar. 2014 and European patent application No. 14162941.0 filed on 31 Mar. 2014. The entire contents of these applications are incorporated herein by reference.

FIELD OF THE INVENTION

The present invention relates generally to mass spectrometry and in particular to methods of screening or testing a sample, methods of mass spectrometry and mass spectrometers.

BACKGROUND

Various mass spectrometry techniques are known which attempt to screen for hemoglobin variants.

For example, TW-201211543 (Wu) discloses a quick screening method for a hemoglobin variant comprising: (a) providing a blood sample; (b) quickly separating hemoglobin from the blood sample; (c) determining whether the resulting product of step (b) contains a hemoglobin variant by using Matrix Assisted Laser Desorption Ionization Time of Flight mass spectrometry (MALDI-TOF) in linear mode, and optionally performing the following steps; (d) enzyme hydrolyzing the resulting product of step (b) under ultrasonic vibration; and (e) determining a type of the hemoglobin variant in the resulting product of step (d) by using MALDI-TOF in reflection mode and applying a comparison software. This method further comprises analyzing partial amino acid sequence of the hemoglobin variant by using tandem mass spectrometry (MS/MS) after performing the step (e).

WO 2004/090552 (Dalton) discloses a screening method using mass spectrometry wherein the ionisation technique produces a multiply-charged spectrum and is used to detect variant peptides, polypeptides and proteins that cause or are indicative of disease. The mass spectrometry is focused on a specific multiply-charged species of the polypeptide of interest, enabling a single targeted ionised species and its corresponding variant (if present) to be measured with greater mass precision. An example of use of this method is a screen for sickle cell disease and sickle cell trait by detecting hemoglobin S and other hemoglobin variants using Electrospray mass spectrometry.

However, the known methods are not clinical diagnostic procedures. WO 2004/090552 (Dalton), for example, explicitly states on page 10, line 29 that "this test is not diagnostic."

Known methods also typically involve complex sample preparation routines. For example, a blood sample may need to be desalted and subjected to liquid chromatography separation which can take a relatively long time to perform.

The article Graça et al., "Electron Transfer Dissociation Mass Spectrometry of Hemoglobin on Clinical Samples", J. Am. Soc. Mass Spectrom. (2012) 23:1750-1756, discloses a method for identifying hemoglobin variants from whole blood using Electron Transfer Dissociation ("ETD") mass spectrometry.

The article Acosta-Martin et al., "Quantitaive Mass Spectrometry Analysis of Intact Hemoglobin A2 by Precursor Ion Isolation and Detection", Anal. Chem. (2013), 85:7971-7975, discloses a method of quantifying hemoglobin using ETD mass spectrometry.

The article Edwards et al., "Top-Down Proteomics and Direct Surface Sampling of Noenatal Dried Blood Spots: Diagnosis of Unknown Hemoglobin Variants", J. Am. Soc. Mass Spectrom. (2012), 23:1921-1930, discloses a method for screening for hemoglobin variants using ETD mass spectrometry.

The techniques described in these articles work with denatured (c.f. native) hemoglobin and therefore require complex sample preparation routines.

Fast methods of obtaining a clinical diagnosis of native hemoglobin variants using mass spectrometry are not known.

It is desired to be able to provide an improved method of screening or testing for native hemoglobin variants using mass spectrometry.

SUMMARY

According to an aspect there is provided a method of screening or testing a sample comprising:

ionising a native human hemoglobin sample to generate parent or precursor ions;

subjecting the parent or precursor ions to Electron Transfer Dissociation fragmentation so as to generate a plurality of fragment ions;

mass analysing the fragment ions; and determining whether or not the fragment ions include fragment ions which are indicative of a variant of hemoglobin.

An embodiment relates to a clinical diagnostic procedure for the testing of native hemoglobin variants from blood samples. The procedure according to an embodiment requires minimal sample preparation since the method works with the native form of hemoglobin. This is in contrast with the known techniques, such as those disclosed in the articles by Graça et al., Acosta-Martin et al., and Edwards et al., which all work with denatured (c.f. native) haemoglobin and hence require complex sample preparation routines.

The term "native human hemoglobin" sample should be understood as meaning a non-denatured haemoglobin sample i.e. a natural or diluted blood sample.

The blood sample may comprise a whole blood sample or a substantially untreated blood sample.

According to an embodiment the sample may be dissolved in a non-denaturant.

The blood sample may be dissolved in a substantially neutral buffer such as a phosphate buffer, a citrate buffer, an acetate buffer, a citrate-phosphate buffer or Tris-HCl. In contrast with acidic buffers, such as buffers that include formic acid ("FA") substantially neutral buffers are typically not denaturants.

According to an embodiment the substantially neutral buffer may comprise ammonium acetate.

According to an embodiment the native or natural human hemoglobin sample is not dissolved in an organic solvent as is commonly used with a liquid chromatography system. Organic solvents, such as acetonitrile ("ACN") and methanol, are typically denaturants.

Electron Transfer Dissociation fragmentation of the non-covalently grouped tetramers of hemoglobin advantageously provides precise determination of hemoglobin variants in an automated procedure.

An embodiment is distinguished from conventional approaches in that the method utilises the natural form of the hemoglobin and utilises Electron Transfer Dissociation (rather than Collision Induced Dissociation) to the non-covalently bound precursor or parent hemoglobin ions.

The method according to an embodiment is significantly faster than conventional methods as minimal sample preparation is required. Furthermore, according to an embodiment only 10 μL of blood is required and no desalting or liquid chromatography separation steps are performed or are required.

Furthermore, according to an embodiment, the native hemoglobin mass spectral peaks that are used in the ETD analysis may include the complete protein, and may encompass both pairs of alpha and beta chains. Therefore, according to an embodiment tandem mass spectrometry ("MS/MS") data that covers at least three clinically significant mass spectral peaks may be acquired simultaneously. As such, according to an embodiment it is not necessary to step through different precursor ions. The method in accordance with an embodiment is therefore significantly faster and simpler than techniques that work with denatured hemoglobin.

According to an embodiment, the acquired native hemoglobin mass spectra are simpler (e.g. comprise less charge states) and potentially comprise less chemical noise e.g. when compared with denatured hemoglobin mass spectra.

In addition, native hemoglobin stock solutions that are used in accordance with an embodiment may be more stable and less prone to degradation than denatured haemoglobin solutions.

It will therefore be appreciated that in accordance with an embodiment, a clinical diagnosis can be obtained much quicker than other conventional methods and in a much simpler manner.

According to an embodiment the process of Electron Transfer Dissociation comprises interacting analyte ions with reagent ions, wherein the reagent ions comprise dicyanobenzene, 4-nitrotoluene or azulene reagent ions.

According to an embodiment the step of determining whether or not the fragment ions include fragment ions which are indicative of a variant of hemoglobin further comprises determining whether or not fragment ions having a −30.0 Da mass difference from $\beta^A C_6$ fragment ions having a mass to charge ratio of 694.4 are present.

According to an embodiment the step of determining whether or not the fragment ions include fragment ions which are indicative of a variant of hemoglobin further comprises determining whether or not $\beta^S C_6$ fragment ions having a mass to charge ratio of 664.4 are present.

According to an embodiment the step of determining whether or not the fragment ions include fragment ions which are indicative of a variant of hemoglobin further comprises determining whether or not $\beta^S C_7$ fragment ions having a mass to charge ratio of 793.5 are present.

According to an embodiment the variant of hemoglobin comprises the HbAS (sickle heterozygote) variant of hemoglobin.

The native human hemoglobin sample may comprise intact non-covalently assembled tetramer ($\alpha_2\beta_2$+4haem) of human hemoglobin.

According to another aspect there is provided a method of mass spectrometry comprising a method of screening or testing a sample as described above.

According to another aspect there is provided a method of screening or testing a sample comprising:

ionising a native human hemoglobin sample to generate parent or precursor ions;

subjecting the parent or precursor ions to Electron Transfer Dissociation fragmentation so as to generate a plurality of fragment ions;

mass analysing the fragment ions and obtaining first mass spectral data;

comparing the first mass spectral data with second mass spectral data wherein the second mass spectral data relates to a hemoglobin control sample (HbAA) that has no abnormalities detected; and determining whether or not the first mass spectral data differs from the second mass spectral data so as to indicate that the native hemoglobin sample comprises a hemoglobin variant.

The variant of hemoglobin may comprise the HbAS (sickle heterozygote) variant of hemoglobin.

The method steps are performed in vitro and are not performed on a human body.

The method is performed on a native human hemoglobin sample without the patient who provided the sample being present.

The sample is not returned to a patient.

According to another aspect there is provided a mass spectrometer comprising:

an ion source;

an Electron Transfer Dissociation fragmentation device;

a mass analyser; and a control system arranged and adapted:

(i) to ionise a native human hemoglobin sample to generate parent or precursor ions;

(ii) to subject the parent or precursor ions to Electron Transfer Dissociation fragmentation in the Electron Transfer Dissociation fragmentation device so as to generate a plurality of fragment ions;

(iii) to mass analyse the fragment ions using the mass analyser; and (iv) to determine whether or not the fragment ions include fragment ions which are indicative of a variant of hemoglobin.

According to another aspect there is provided a mass spectrometer comprising:

an ion source;

an Electron Transfer Dissociation fragmentation device;

a mass analyser; and a control system arranged and adapted:

(i) to ionise a native human hemoglobin sample to generate parent or precursor ions;

(ii) to subject the parent or precursor ions to Electron Transfer Dissociation fragmentation in the Electron Transfer Dissociation fragmentation device so as to generate a plurality of fragment ions;

(iii) to mass analyse the fragment ions using the mass analyser so as to obtain first mass spectral data;

(iv) to compare the first mass spectral data with second mass spectral data wherein the second mass spectral data relates to a hemoglobin control sample (HbAA) that has no abnormalities detected; and (v) to determine whether or not the first mass spectral data differs from the second mass spectral data so as to indicate that the native hemoglobin sample comprises a hemoglobin variant.

According to an aspect of there is provided a method of screening or testing a sample comprising:

ionising a sample of whole blood optionally dissolved in a substantially neutral buffer to generate parent or precursor ions;

subjecting the parent or precursor ions to Electron Transfer Dissociation fragmentation so as to generate a plurality of fragment ions;

mass analysing the fragment ions; and determining whether or not the fragment ions include fragment ions which are indicative of a variant of hemoglobin.

The sample may comprise a sample comprising e.g. about ≤1000 μL, about ≤500 μL, about ≤100 μL, about ≤50 μL or about ≤10 μL of whole blood. The sample may comprise a small sample of untreated blood.

The substantially neutral buffer may comprise a phosphate buffer, a citrate buffer, an acetate buffer, a citrate-phosphate buffer or Tris-HCl. According to an embodiment the substantially neutral buffer may comprise ammonium acetate.

According to another embodiment there is provided a mass spectrometer comprising:

an ion source;

an Electron Transfer Dissociation fragmentation device;

a mass analyser; and a control system arranged and adapted:

(i) to ionise a sample of whole blood optionally dissolved in a substantially neutral buffer to generate parent or precursor ions;

(ii) to subject the parent or precursor ions to Electron Transfer Dissociation fragmentation in the Electron Transfer Dissociation fragmentation device so as to generate a plurality of fragment ions;

(iii) to mass analyse the fragment ions using the mass analyser; and (iv) to determine whether or not the fragment ions include fragment ions which are indicative of a variant of hemoglobin.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation may comprise interacting analyte ions with reagent ions, wherein the reagent ions comprise dicyanobenzene, 4-nitrotoluene or azulene reagent ions.

According to an embodiment ions may be subjected to Electron Transfer Dissociation in an ion guide, ion-ion reaction device or ion-neutral gas reaction device which may comprise a plurality of electrodes having one or more apertures through which ions are transmitted in use. A pattern or series of digital voltage pulses may be applied to the electrodes in use. The digital voltage pulses may be applied in a stepped sequential manner and may be sequentially applied to the electrodes. A first DC travelling wave or series of transient DC voltages or potentials may be arranged to move in time from a first (upstream) end of the ion guide, ion-ion reaction device or ion-neutral gas reaction device towards the middle of the ion guide, ion-ion reaction device or ion-neutral gas reaction device.

According to an embodiment at the same time, a second DC travelling wave or series of transient DC voltages or potentials may optionally be arranged to move in time from a second (downstream) end of the ion guide, ion-ion reaction device or ion-neutral gas reaction device also towards the middle of the ion guide, ion-ion reaction device or ion-neutral gas reaction device. As a result, the two DC travelling waves or series of transient DC voltages or potentials may converge from opposite sides of the ion guide, ion-ion reaction device or ion-neutral gas reaction device towards the middle or central region of the ion guide, ion-ion reaction device or ion-neutral gas reaction device.

The intensity or amplitude of the digital pulses applied to the electrodes may be arranged to reduce towards the middle or centre of the ion guide, ion-ion reaction device or ion-neutral gas reaction device. As a result, the intensity or amplitude of the digital voltage pulses which may be applied to electrodes which are close to the input or exit regions or ends of the ion guide, ion-ion reaction device or ion-neutral gas reaction device may be greater than the intensity or amplitude of the digital voltage pulses which may be applied to electrodes in the central region of the ion guide, ion-ion reaction device or ion-neutral gas reaction device.

Other embodiments are contemplated wherein the amplitude of the transient DC voltages or potentials or the digital voltage pulses which may be applied to the electrodes does not reduce with axial displacement along the length of the ion guide, ion-ion reaction device or ion-neutral gas reaction device. According to this embodiment the amplitude of the digital voltages pulses remains substantially constant with axial displacement along the length of the ion guide, ion-ion reaction device or ion-neutral gas reaction device.

The voltage pulses which may be applied to the lens elements or ring electrodes of the ion guide, ion-ion reaction device or ion-neutral gas reaction device may be square waves. The electric potential within the ion guide, ion-ion reaction device or ion-neutral gas reaction device may relax so that the wave function potential within the ion guide, ion-ion reaction device or ion-neutral gas reaction device may take on a smooth function.

According to an embodiment analyte cations (e.g. positively charged analyte ions) and/or reagent anions (e.g. negatively charged reagent ions) may be simultaneously introduced into the ion guide, ion-ion reaction device or ion-neutral gas reaction device from opposite ends of the ion guide, ion-ion reaction device or ion-neutral gas reaction device. Once in the ion guide, ion-ion reaction device or ion-neutral gas reaction device, positive ions (cations) may be repelled by the positive (crest) potentials of the DC travelling wave or the one or more transient DC voltages or potentials which may be applied to the electrodes of the ion guide, ion-ion reaction device or ion-neutral gas reaction device. As the electrostatic travelling wave moves along the length of the ion guide, ion-ion reaction device or ion-neutral gas reaction device, the positive ions may be pushed along the ion guide, ion-ion reaction device or ion-neutral gas reaction device in the same direction as the travelling wave.

Negatively charged reagent ions (i.e. reagent anions) will be attracted towards the positive potentials of the travelling wave and will likewise be drawn, urged or attracted in the direction of the travelling wave as the travelling DC voltages or potentials move along the length of the ion guide, ion-ion reaction device or ion-neutral gas reaction device. As a result, whilst positive ions may travel in the negative crests (positive valleys) of the travelling DC wave, negative ions may travel in the positive crests (negative valleys) of the travelling DC wave or the one or more transient DC voltages or potentials.

According to an embodiment two opposed travelling DC waves may be arranged to translate ions substantially simultaneously towards the middle or centre of the ion guide, ion-ion reaction device or ion-neutral gas reaction device from both ends of the ion guide, ion-ion reaction device or ion-neutral gas reaction device. The travelling DC waves may be arranged to move towards each other and can be considered as effectively converging or coalescing in the central region of the ion guide, ion-ion reaction device or ion-neutral gas reaction device. Cations and anions may be simultaneously carried towards the middle of the ion guide, ion-ion reaction device or ion-neutral gas reaction device. Other embodiments are contemplated wherein analyte cations may be simultaneously introduced from different ends of the reaction device. According to this embodiment the analyte ions may be reacted with neutral reagent gas present within the reaction device or which is added subsequently to the reaction device. According to another embodiment two different species of reagent ions may be introduced (simultaneously or sequentially) into the reaction device from different ends of the reaction device.

According to an embodiment cations may be translated towards the centre of the ion guide, ion-ion reaction device or ion-neutral gas reaction device by a first travelling DC wave and anions may be translated towards the centre of the ion guide, ion-ion reaction device or ion-neutral gas reaction device by a second different travelling DC wave.

However, other embodiments are contemplated wherein both cations and anions may be simultaneously translated by a first DC travelling wave towards the centre (or other region) of the ion guide, ion-ion reaction device or ion-neutral gas reaction device. According to this embodiment cations and/or anions may also optionally be simultaneously translated towards the centre (or other region) of the ion guide, ion-ion reaction device or ion-neutral gas reaction device by a second DC travelling voltage wave. So for example, according to an embodiment anions and cations may be simultaneously translated by a first DC travelling wave in a first direction at the same time as other anions and cations are simultaneously translated by a second DC travelling wave which may move in a second direction which may be opposed to the first direction.

According to an embodiment as ions approach the middle or central region of the ion guide, ion-ion reaction device or ion-neutral gas reaction device, the propelling force of the travelling waves may be programmed to diminish and the amplitude of the travelling waves in the central region of the ion guide, ion-ion reaction device or ion-neutral gas reaction device may be arranged to become effectively zero or is otherwise at least significantly reduced. As a result, the valleys and peaks of the travelling waves may effectively disappear (or are otherwise significantly reduced) in the middle (centre) of the ion guide, ion-ion reaction device or ion-neutral gas reaction device so that according to an embodiment ions of opposite polarity (or alternatively of the same polarity) may then be allowed or caused to merge and interact with each other within the central region of the ion guide, ion-ion reaction device or ion-neutral gas reaction device. If any ions stray randomly axially away from the middle or central region of the ion guide, ion-ion reaction device or ion-neutral gas reaction device due, for example, to multiple collisions with buffer gas molecules or due to high space charge effects, then these ions may then encounter subsequent travelling DC waves which may have the effect of translating or urging the ions back towards the centre of the ion guide, ion-ion reaction device or ion-neutral gas reaction device.

According to an embodiment positive analyte ions may be arranged to be translated towards the centre of the ion guide, ion-ion reaction device or ion-neutral gas reaction device by a first DC travelling wave which is arranged to move in a first direction and negative reagent ions may be arranged to be translated towards the centre of the ion guide, ion-ion reaction device or ion-neutral gas reaction device by a second DC travelling wave which is arranged to move in a second direction which is opposed to the first direction.

According to other embodiments instead of applying two opposed DC travelling waves to the electrodes of the ion guide, ion-ion reaction device or ion-neutral gas reaction device a single DC travelling wave may instead be applied to the electrodes of the ion guide, ion-ion reaction device or ion-neutral gas reaction device at any particular instance in time. According to this embodiment negatively charged reagent ions (or alternatively positively charged analyte ions) may first be loaded or directed into the ion guide, ion-ion reaction device or ion-neutral gas reaction device. The reagent anions may be translated from an entrance region of the ion guide, ion-ion reaction device or ion-neutral gas reaction device along and through the ion guide, ion-ion reaction device or ion-neutral gas reaction device by a DC travelling wave. The reagent anions may be retained within the ion guide, ion-ion reaction device or ion-neutral gas reaction device by applying a negative potential at the opposite end or exit end of the ion guide, ion-ion reaction device or ion-neutral gas reaction device.

After reagent anions (or alternatively analyte cations) have been loaded into the ion guide, ion-ion reaction device or ion-neutral gas reaction device, positively charged analyte ions (or alternatively negatively charged reagent ions) may then be translated along and through the ion guide, ion-ion reaction device or ion-neutral gas reaction device by a DC travelling wave or a plurality of transient DC voltages or potentials applied to the electrodes.

The DC travelling wave which translates the reagent anions and the analyte cations may comprise one or more transient DC voltage or potentials or one or more transient DC voltage or potential waveforms which may be applied to the electrodes of the ion guide, ion-ion reaction device or ion-neutral gas reaction device. The parameters of the DC travelling wave and in particular the speed or velocity at which the transient DC voltages or potentials are applied to the electrodes along the length of the ion guide, ion-ion reaction device or ion-neutral gas reaction device may be varied or controlled in order to optimise, maximise or minimise ion-ion reactions between the negatively charged reagent ions and the positively charged analyte ions.

Fragment or product ions which result from the ion-ion interactions may be swept out of the ion guide, ion-ion reaction device or ion-neutral gas reaction device, in an embodiment by a DC travelling wave and in an embodiment before the fragment or product ions can be neutralised. Unreacted analyte ions and/or unreacted reagent ions may also be removed from the ion guide, ion-ion reaction device or ion-neutral gas reaction device, in an embodiment by a DC travelling wave, if so desired. The negative potential which may be applied across at least the downstream end of the ion guide, ion-ion reaction device or ion-neutral gas reaction device may also act to accelerate positively charged product or fragment anions out of the ion guide, ion-ion reaction device or ion-neutral gas reaction device.

According to an embodiment a negative potential may optionally be applied to one or both ends of the ion guide, ion-ion reaction device or ion-neutral gas reaction device in order to retain negatively charged ions within the ion guide, ion-ion reaction device or ion-neutral gas reaction device. The negative potential which is applied may also have the effect of encouraging or urging positively charged fragment or product ions which are created or formed within the ion guide, ion-ion reaction device or ion-neutral gas reaction device to exit the ion guide, ion-ion reaction device or ion-neutral gas reaction device via one or both ends of the ion guide, ion-ion reaction device or ion-neutral gas reaction device.

According to an embodiment positively charged fragment or product ions may be arranged to exit the ion guide, ion-ion reaction device or ion-neutral gas reaction device after approximately 30 ms from formation thereby avoiding neutralisation of the positively charged fragment or product ions within the ion guide, ion-ion reaction device or ion-neutral gas reaction device. However, other embodiments are contemplated wherein the fragment or product ions formed within the ion guide, ion-ion reaction device or ion-neutral gas reaction device may be arranged to exit the ion guide, ion-ion reaction device or ion-neutral gas reaction device more quickly e.g. within a timescale of about 0-10 ms, about 10-20 ms or about 20-30 ms.

Alternatively, the fragment or product ions formed within the ion guide, ion-ion reaction device or ion-neutral gas reaction device may be arranged to exit the ion guide, ion-ion reaction device or ion-neutral gas reaction device more slowly e.g. within a timescale of about 30-40 ms, about 40-50 ms, about 50-60 ms, about 60-70 ms, about 70-80 ms, about 80-90 ms, about 90-100 ms or about >100 ms.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer may further comprise a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described together with other arrangements given for illustrative purposes only, by way of example only, and with reference to the accompanying drawings in which.

DETAILED DESCRIPTION

A conventional approach to analysing hemoglobin will first be described.

Normal adult human hemoglobin (Hb) exists as a non-covalently assembled tetramer consisting of two alpha chains (MW 15,126.4) and two beta-chains (15,867.2) in which each chain is associated with a heme group (MW 616.5). The average molecular weight of the intact assembly is 66,453.2. The primary function of hemoglobin is to deliver oxygen to the organs of the body. Structural abnormalities within the sequence of one of these chains can affect the overall function of the assembled hemoglobin tetramer.

In adult human hemoglobin approximately 1000 alpha- and beta-chain abnormalities (variants) have been described and many more are possible.

Hemoglobin variants are generally caused by a single base mutation in a globin gene. Some variants are clinically significant whilst many function normally. Knowledge of how each type of change specifically alters the function is important in understanding how hemoglobin works as well as for treating diseases caused by hemoglobin variants.

Figure 1:
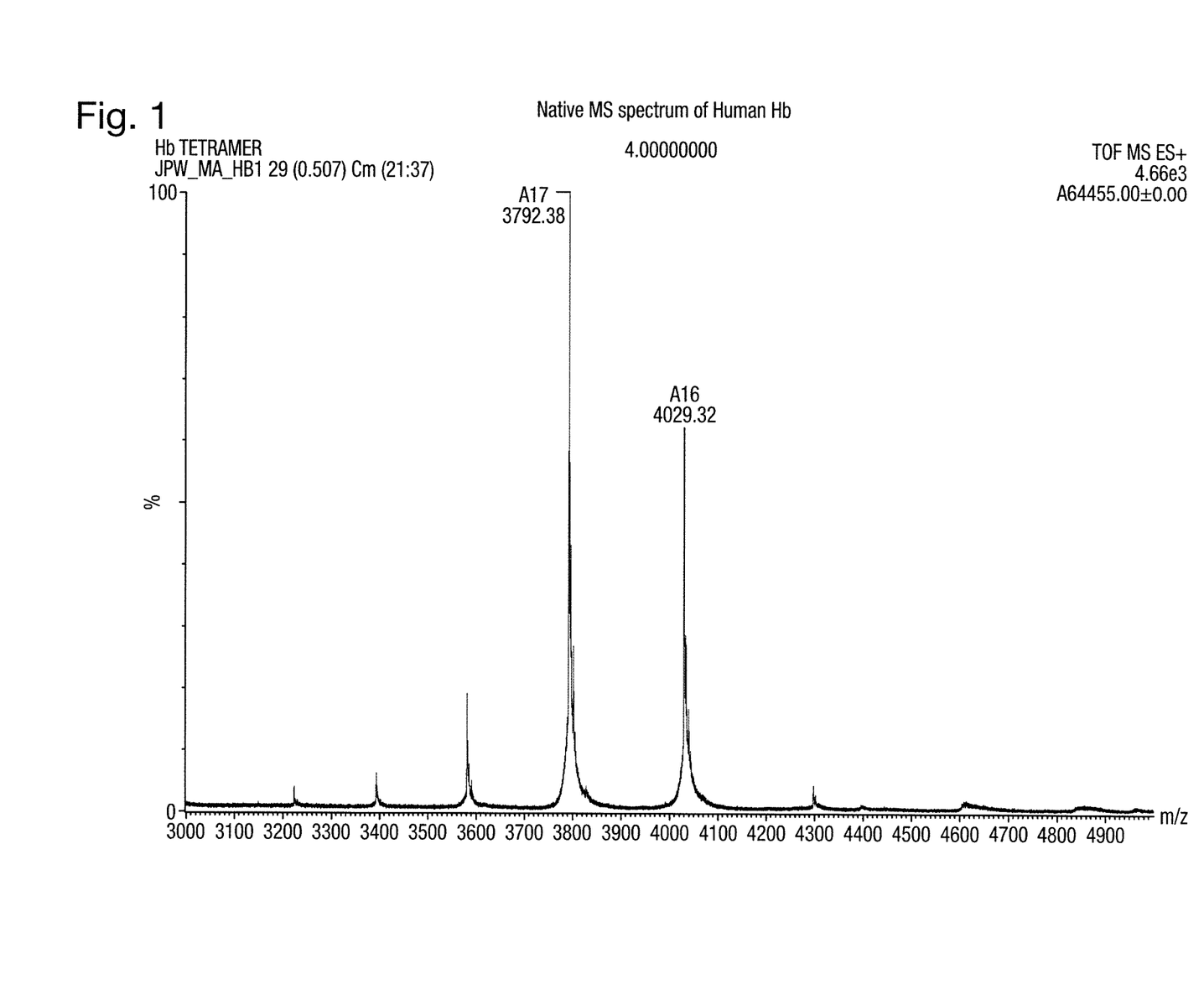
FIG. 1 shows a mass spectrum of native human hemoglobin.

FIG. 1 shows a parent ion mass spectrum of native human hemoglobin showing multiply charged ions detected ranging from $[M+15H]^{15+}$ to $[M+20H]^{20+}$.

Figure 2:
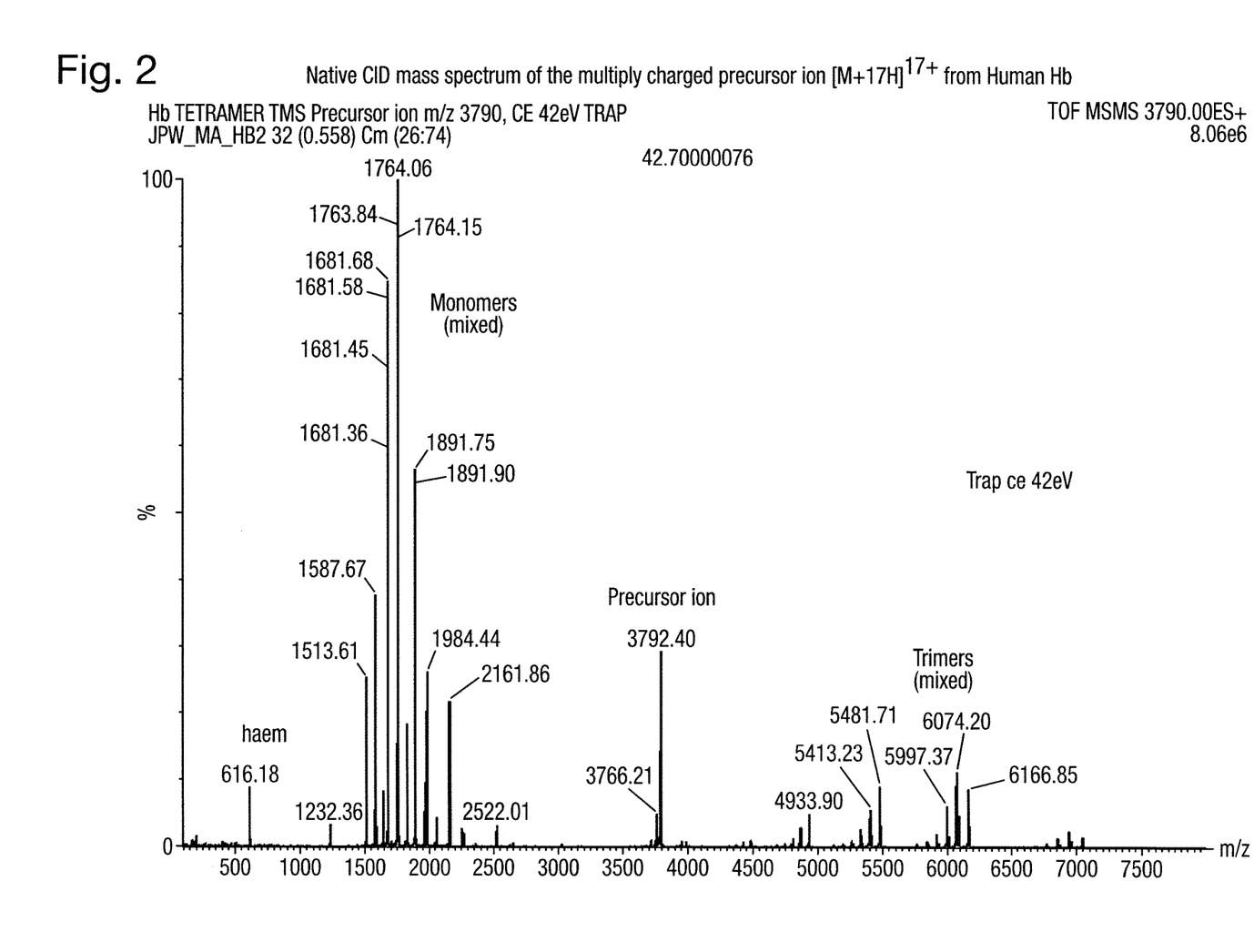
FIG. 2 shows a fragmentation spectrum of the fragment ions obtained from subjecting $[M+17H]^{17+}$ parent ions of human hemoglobin to Collision Induced Dissociation.

FIG. 2 shows a fragmentation mass spectrum obtained by subjecting multiply charged precursor ions $[M+17H]^{17+}$ of human hemoglobin to Collision Induced Dissociation fragmentation. Following ejection of an alpha- or beta-chain sub-unit, mixed trimeric species ($\alpha_2\beta$ and $\alpha\beta_2$) are detected with and without the heme group. Sub-unit loss is observed following Collision Induced Dissociation and little, if any, sequence-specific information is obtained unless more complex experiments such as $MS^3$ or higher are performed.

An embodiment will now be described.

The embodiment described below relates to methodologies involving the Electron Transfer Dissociation analysis of native hemoglobin clinical samples in order to provide a clinical diagnosis.

Electrospray ionisation combined with Electron Transfer Dissociation of selected multiply charged precursor ions produced from the intact non-covalently assembled tetramer ($\alpha_2\beta_2$+4haem) of human hemoglobin is able to rapidly identify examples of human hemoglobin variants.

Electron Transfer Dissociation fragmentation method provides a rapid non-ergodic reaction of selected positive multiply charged ions with radical anions and causes extensive cleavage of the peptide backbone.

Figure 3A:
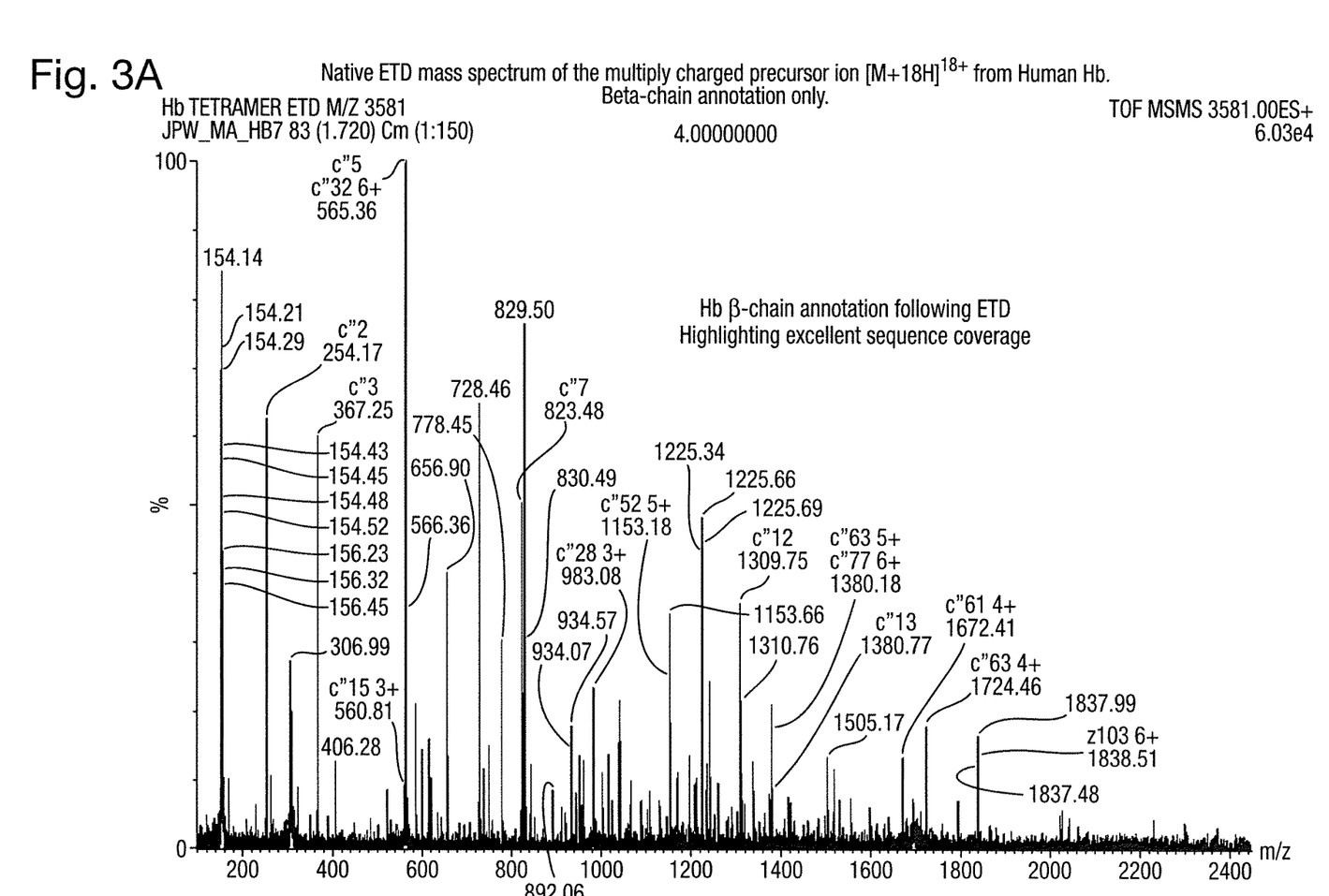
FIG. 3A shows an Electron Transfer Dissociation mass spectrum of $[M+18H]^{18+}$ parent ions of human hemoglobin showing beta-chain annotation and FIG. 3B shows the same Electron Transfer Dissociation mass spectrum of $[M+18H]^{18+}$ parent ions from human hemoglobin but showing alpha-chain annotation.
Figure 3B:
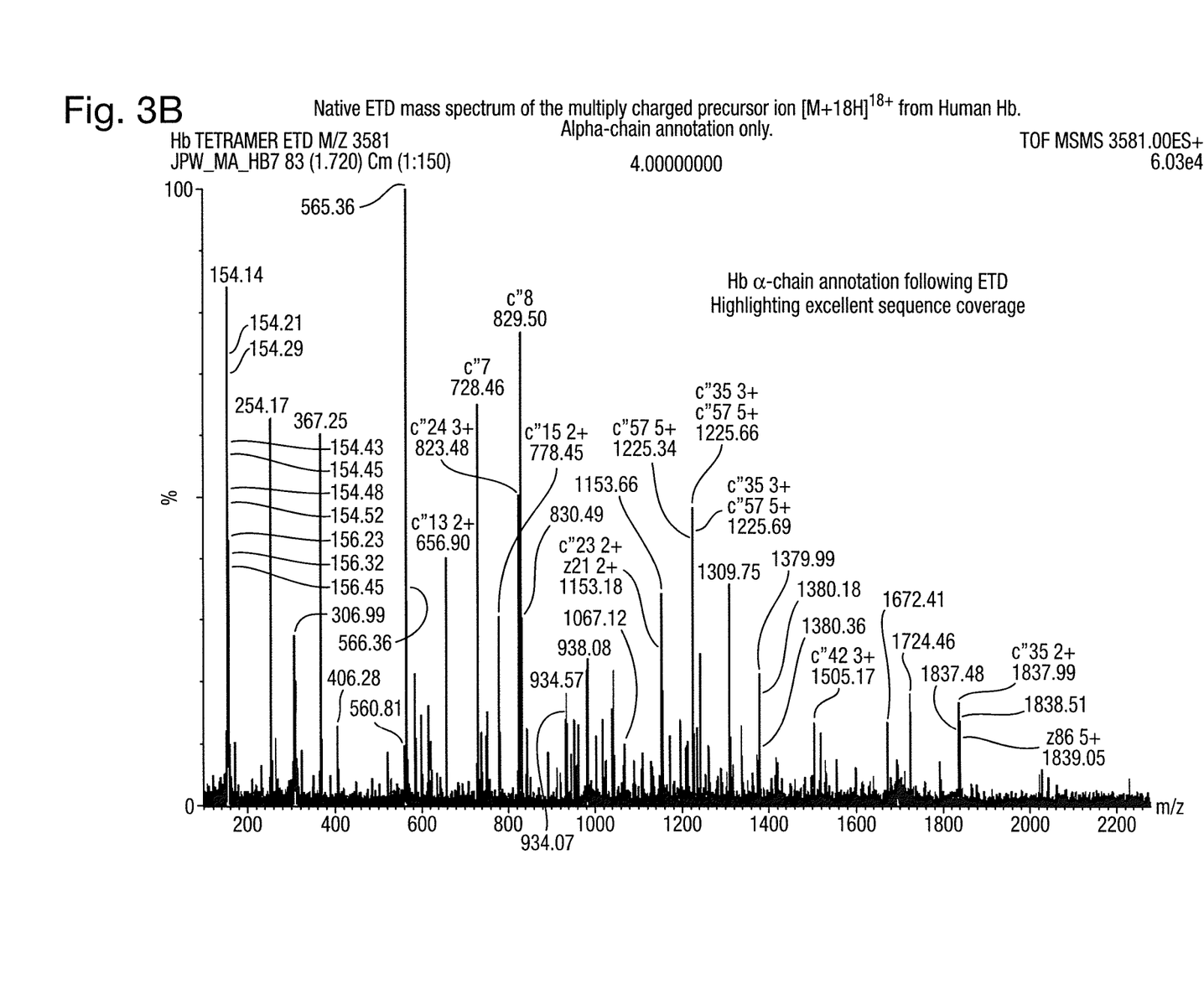

FIGS. 3A and 3B show an Electron Transfer Dissociation mass spectrum of multiply charged precursor ions $[M+18H]^{18+}$ from human haemoglobin obtained using 4-nitrotoluene as the ETD reagent ions. The mass spectra shown in FIGS. 3A and 3B are the same but the mass spectra have been separately annotated with alpha- and beta-chain notation.

It is clear that extensive sequence-specific information is provided through the use of Electron Transfer Dissociation fragmentation compared to Collision Induced Dissociation fragmentation and highlights the ability of Electron Transfer Dissociation and subsequent mass analysis of human hemoglobin in order to identify or detect hemoglobin variants.

Figure 4:
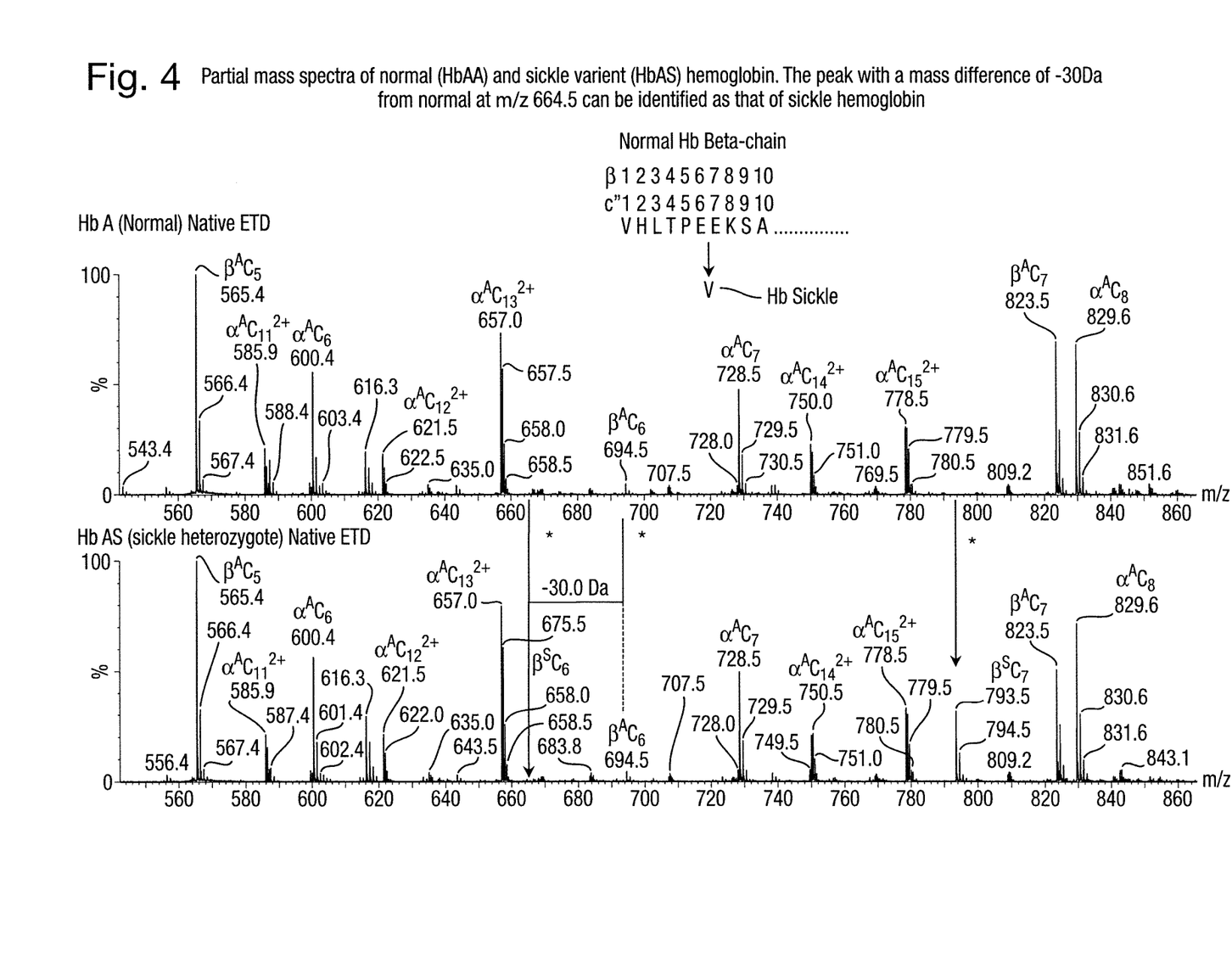
FIG. 4 shows partial mass spectra of normal (HbAA) and the sickle variant (HbAS) of hemoglobin obtained according to an embodiment and wherein the peak at mass to charge ratio 664.4 having a mass difference of −30 Da relative to the fragment mass peak at 694.4 is indicative that the hemoglobin sample comprises the sickle variant of hemoglobin.

FIG. 4 shows an example of the identification of HbAS (sickle heterozygote) using native or natural hemoglobin which is present in a blood sample and top-down Electron Transfer Dissociation mass spectrometry obtained using 4-nitrotoluene as the ETD reagent ions. The mass spectral data may be compared with a normal hemoglobin control (HbAA) that has no abnormalities detected.

The hemoglobin sickle variant (HbAS or HbSS), β6Glu (E)→Val (V), can be identified by various phenotypic methods. Identification can be questioned when the sickle variant in a heterozygote is significantly different from its normal value (~40%). Therefore, DNA analysis or confirmation by mass spectrometry is required.

Mass spectrometry is fast and using the method according to an embodiment enables protein sequence information to be rapidly used to determine HbAS or HbSS for example. Other clinically significant and or innocuous variants can also be identified using the technique according to an embodiment.

FIG. 4 shows the partial mass spectra obtained from native top-down Electron Transfer Dissociation mass spectrometry of a normal hemoglobin (HbAA) and a sickle variant hemoglobin heterozygote (HbAS).

Figure 5:
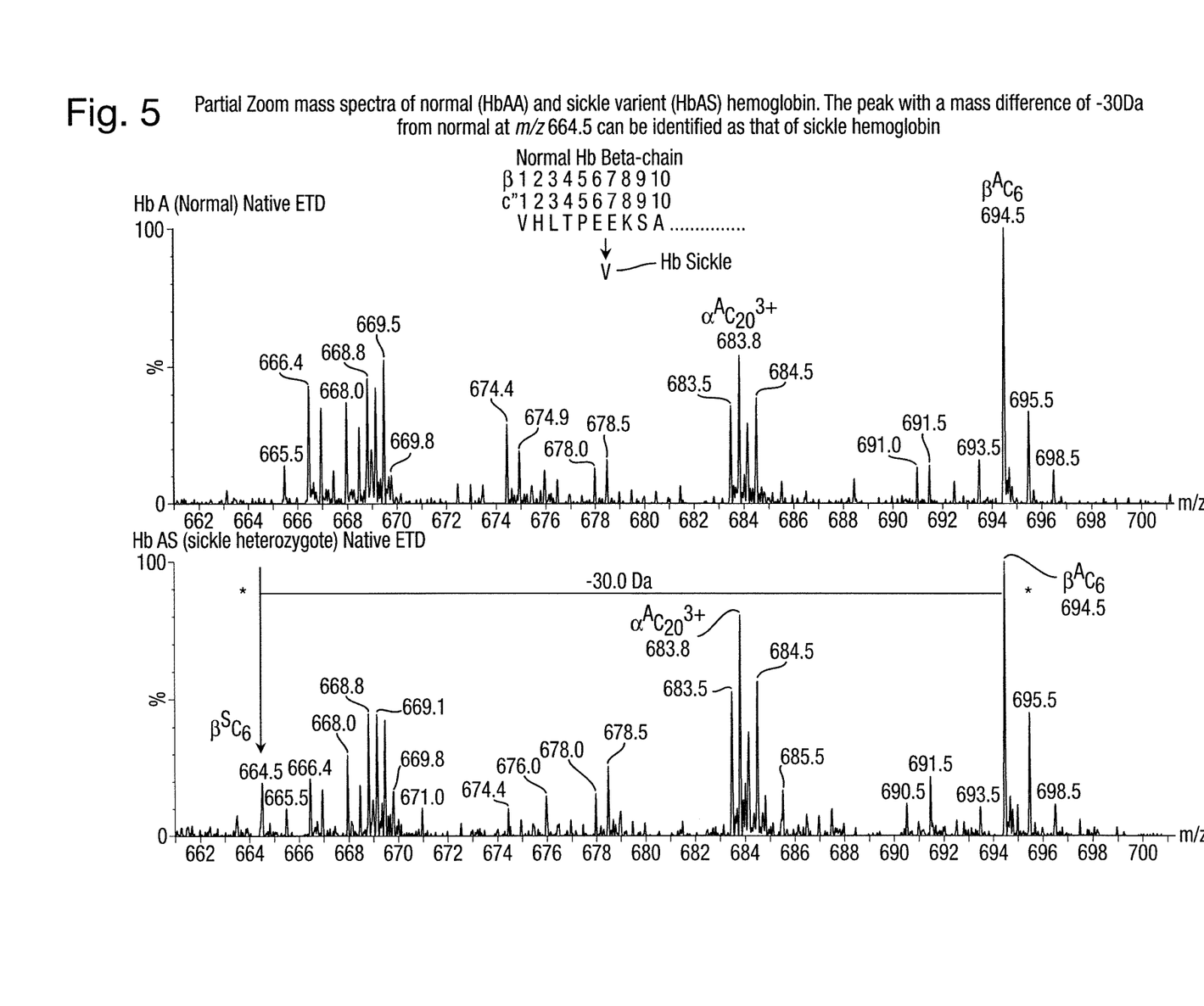
FIG. 5 shows in greater detail partial mass spectra of normal (HbAA) and the sickle variant (HbAS) of hemoglobin.

FIG. 5 shows in greater detail the partial mass spectra highlighting a −30.0 Da mass difference at position c6 in the beta-chain from normal. This data precisely shows the ability of hemoglobin phenotyping using the method according to an embodiment.

The samples were analysed as received and diluted for Electrospray ionisation-mass spectrometry analysis to a concentration of ~10 μM (100 mM ammonium acetate) without any prior work up or de-salting procedures.

Although the present invention has been described with reference to preferred embodiments, it will be understood by those skilled in the art that various changes in form and detail may be made without departing from the scope of the present invention as set forth in the accompanying claims.

The invention claimed is:

1. A method of screening or testing a sample comprising:
    ionising a native human non-denatured hemoglobin sample to generate parent or precursor ions, wherein said sample is a non-denatured whole blood sample diluted with a non-denaturant, and wherein said sample has not been desalted;
    subjecting said parent or precursor ions to Electron Transfer Dissociation fragmentation so as to generate a plurality of fragment ions;
    mass analysing said fragment ions; and
    determining whether or not said fragment ions include fragment ions which are indicative of a variant of hemoglobin.

2. A method as claimed in claim 1, wherein the step of determining whether or not said fragment ions include fragment ions which are indicative of a variant of hemoglobin further comprises determining whether or not fragment ions having a −30.0 Da mass difference from $\beta^A c_6$ fragment ions having a mass to charge ratio of 694.4 are present.

3. A method as claimed in claim 1, wherein the step of determining whether or not said fragment ions include fragment ions which are indicative of a variant of hemoglobin further comprises determining whether or not $\beta^S c_6$ fragment ions having a mass to charge ratio of 664.4 are present.

4. A method as claimed in claim 1, wherein the step of determining whether or not said fragment ions include fragment ions which are indicative of a variant of hemoglobin further comprises determining whether or not $\beta^S c_7$ fragment ions having a mass to charge ratio of 793.5 are present.

5. A method as claimed in claim 1, wherein said variant of hemoglobin comprises the HbAS (sickle heterozygote) variant of hemoglobin.

6. A method as claimed in claim 1, wherein said native human hemoglobin sample comprises intact non-covalently assembled tetramer of human hemoglobin.

7. A method as claimed in claim 1, wherein said method steps are performed in vitro and are not performed on a human body.

8. A method as claimed in claim 1, wherein said method is performed on a native human hemoglobin sample without the patient who provided said sample being present.

9. A method as claimed in claim 1, wherein said sample is not returned to a patient.

10. A method as claimed in claim 1, wherein said step of ionising said native human hemoglobin sample comprises ionising a sample of whole blood dissolved in a neutral buffer to generate parent or precursor ions.

11. A method as claimed in claim 10, wherein said sample comprises ≤1000 μL, ≤500 μL, ≤100 μL, ≤50 μL or ≤10 μL of whole blood.

12. A method as claimed in claim 1, wherein said non-denaturant is a neutral buffer comprising a phosphate buffer, a citrate buffer, an acetate buffer, a citrate-phosphate buffer or Tris-HCl.

13. A method as claimed in claim 12, wherein said non-denaturant is a neutral buffer comprising ammonium acetate.

14. A method as claimed in claim 1, wherein said sample is not diluted with formic acid.

15. A method as claimed in claim 1, wherein said sample is not diluted with an organic solvent.

16. A method of screening or testing a sample comprising:
    ionising a native human non-denatured hemoglobin sample to generate parent or precursor ions, wherein said sample is a non-denatured whole blood sample diluted with a non-denaturant and wherein said sample has not been desalted;
    subjecting said parent or precursor ions to Electron Transfer Dissociation fragmentation so as to generate a plurality of fragment ions;
    mass analysing said fragment ions and obtaining first mass spectral data;
    comparing said first mass spectral data with second mass spectral data wherein said second mass spectral data relates to a hemoglobin control sample (HbAA) that has no abnormalities detected; and
    determining whether or not said first mass spectral data differs from said second mass spectral data so as to indicate that said native hemoglobin sample comprises a hemoglobin variant.

17. A method as claimed in claim 16, wherein said variant of hemoglobin comprises the HbAS (sickle heterozygote) variant of hemoglobin.

18. A method of mass spectrometry comprising a method of screening or testing a sample as claimed in claim 1.

* * * * *